United States Patent
Clayton (10) Patent No.: US 10,398,571 B1
(45) Date of Patent: Sep. 3, 2019

(54) PROTECTIVE COVER FOR A PROSTHETIC IMPLANT

(71) Applicant: Matthew D. Clayton, Hampton Cove, AL (US)

(72) Inventor: Matthew D. Clayton, Hampton Cove, AL (US)

(*) Notice: Subject to any disclaimer, the term of this patent is extended or adjusted under 35 U.S.C. 154(b) by 0 days.

(21) Appl. No.: 16/261,439

(22) Filed: Jan. 29, 2019

(51) Int. Cl.
*A61F 2/46* (2006.01)
*A61F 2/34* (2006.01)
*A61F 2/00* (2006.01)
*A61F 2/30* (2006.01)

(52) U.S. Cl.
CPC .......... *A61F 2/4609* (2013.01); *A61F 2/0095* (2013.01); *A61F 2/34* (2013.01); *A61F 2002/30016* (2013.01); *A61F 2002/3025* (2013.01); *A61F 2002/30115* (2013.01); *A61F 2002/30247* (2013.01); *A61F 2002/4623* (2013.01); *A61F 2002/4679* (2013.01)

(58) Field of Classification Search
CPC ...... A61F 2/0095; A61F 2/34; A61F 2/30721; A61B 17/025; A61B 2017/0275; A61B 2/1659; B65B 3/262; B65B 3/264; B65B 3/266–268; B65B 83/00; B65B 83/0055; B65B 85/00; B65B 85/1018

See application file for complete search history.

(56) References Cited

U.S. PATENT DOCUMENTS

| | | | |
|---|---|---|---|
| 3,818,514 A | 6/1974 | Clark | |
| 6,432,141 B1* | 8/2002 | Stocks | A61F 2/30742 623/22.13 |
| 6,746,452 B2 | 6/2004 | Tuke et al. | |
| 6,863,692 B2* | 3/2005 | Meulink | A61F 2/0095 206/363 |
| 8,790,413 B2* | 7/2014 | Meulink | A61F 2/0095 623/23.46 |
| 9,248,021 B1* | 2/2016 | Termanini | A61F 2/30721 |
| 9,615,927 B2* | 4/2017 | Huff | A61F 2/3609 |
| 10,201,428 B2* | 2/2019 | Huff | A61F 2/3609 |
| 2003/0191537 A1* | 10/2003 | Wasielewski | A61F 2/30721 623/22.11 |

(Continued)

FOREIGN PATENT DOCUMENTS

EP 0 738 503 A1 10/1996

*Primary Examiner* — Alvin J Stewart (74) *Attorney, Agent, or Firm* — Eric B. Fugett; Mark A. Pitchford; Pitchford Fugett, PLLC (57) ABSTRACT

A protective cover for a prosthetic implant is a flexible body defining an interior space in which a prosthetic implant is receivable. The body includes a lip and an area of weakness formed in one side of the body extending from the lip to a central (i.e., top) portion of the body. The cover can also include an elongated tab extending from a side of the body opposite the slit. The cover covers an exterior surface of the implant when the implant is received in the interior space and thereby prevents soft tissues through which the implant is advanced during surgical introduction of the implant into a joint of patient from contacting and becoming adherent to the exterior surface of the implant. The cover can be extracted and the implant released from the interior space through the area of weakness and into the joint by applying a pulling force to a side of the body opposite the area of weakness.

20 Claims, 10 Drawing Sheets

(56) References Cited

U.S. PATENT DOCUMENTS

| | | | | |
|---|---|---|---|---|
| 2004/0015238 A1* | 1/2004 | Buehler | ............. | A61B 17/8808 |
| | | | | 623/22.12 |
| 2004/0098134 A1* | 5/2004 | Meulink | ............... | A61F 2/0095 |
| | | | | 623/23.52 |
| 2007/0100464 A1* | 5/2007 | Meulink | ............... | A61F 2/0095 |
| | | | | 623/23.46 |
| 2008/0234688 A1* | 9/2008 | Johnson | ............... | A61B 17/025 |
| | | | | 606/91 |
| 2011/0155592 A1* | 6/2011 | Liccardo | ............... | A61F 2/0095 |
| | | | | 206/210 |
| 2011/0218639 A1* | 9/2011 | Shea | ................... | A61F 2/30721 |
| | | | | 623/22.26 |
| 2015/0230926 A1* | 8/2015 | Smith | ................... | A61F 2/0095 |
| | | | | 623/18.11 |
| 2016/0038131 A1* | 2/2016 | White | ................... | A61B 90/08 |
| | | | | 606/90 |
| 2016/0106507 A1* | 4/2016 | Richart | ................. | A61F 2/0095 |
| | | | | 206/484 |
| 2016/0374720 A1* | 12/2016 | Anderson | .......... | A61B 17/3468 |
| | | | | 623/8 |
| 2017/0027708 A1* | 2/2017 | Shenoy | ................. | A61B 17/56 |

* cited by examiner

PROTECTIVE COVER FOR A PROSTHETIC IMPLANT

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

Not Applicable.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND OF THE INVENTION

The present disclosure relates generally to arthroplasty and prosthetic implants, and more particularly, to a protective cover for a prosthetic implant that prevents soft tissues through which the implant is advanced during surgical introduction of the implant into a joint of a patient from contacting and becoming adherent to an exterior surface of the implant.

Hip replacement is one of the most common orthopedic procedures performed in the United States today. Total hip replacement generally involves replacing both the head of the femur (i.e., femoral head) and the acetabulum (i.e., cotyloid cavity) of the pelvis with a prosthetic implant. The prosthetic acetabulum is known in the art as an "acetabular cup" and typically consists of a generally hemispherical body having a porous, convex exterior or back surface (which can be a separate shell) and a smooth, concave interior surface (which can be a separate liner or insert). During hip replacement surgery, the acetabular cup is inserted through the soft tissue surrounding the hip and into the acetabulum where it obtains stability via intimate contact between the porous back surface of the cup and the bone of the patient. Unfortunately, as the acetabular cup is being advanced down into the acetabulum, inevitable contact between the porous exterior surface of the cup and surrounding soft tissues can damage these tissues and cause tissue to become adherent to the exterior surface of the cup, which decreases the likelihood of desirable bony ingrowth into the cup and successful osseointegration of the implant.

Accordingly, what is needed are improvements in surgical tools for use with prosthetic implants and surgical techniques for introducing a prosthetic implant into a patient.

BRIEF SUMMARY

Aspects of the present disclosure overcome or minimize some or all of the shortcomings of the prior art by providing a surgical tool in the form of a protective cover for a prosthetic implant that covers an exterior surface of the implant during surgical introduction of the implant into a joint socket or other bony portion of a patient and thereby prevents soft tissues through which the implant is advanced from contacting and becoming adherent to the exterior surface of the implant.

In one aspect, a protective cover for a prosthetic implant includes a flexible body having a central portion, a lip, an exterior surface, and an interior surface. The interior surface defines an interior space in which a prosthetic implant is receivable. The interior surface can include a curvature that is complimentary to a curvature of an exterior surface of the implant. An area of weakness, which can be a line having a thinned cross section, a slit or a series of perforations formed in a side of the body, extends along a curvature of the body upward from the lip into the central portion. The body is sized and shaped to cover substantially all of an exterior surface of the prosthetic implant when the implant is received in the interior space. In this way, the cover prevents substantially all the exterior surface of the implant from contacting soft tissues through which the implant is advanced while the implant is received in the cover during surgical introduction of the implant into a joint socket or other bony cavity of a patient.

The cover can be extracted from the patient and the implant simultaneously released from the cover by applying a pulling force to a side of the body opposite the line of weakness. The application of a pulling force in a direction away from the joint causes the flexible body to deform and the line of weakness to open around the implant as the cover is pulled over the implant and out of the joint.

To facilitate manual extraction of the protective cover from a joint or other implant site without the use of a clamping instrument, in some embodiments, the protective cover can also include an elongated tab extending from a portion of a side of the body opposite the area of weakness. The portion of the body from which the tab extends can be a portion of the lip opposite the area of weakness. The tab can include a proximate end connected to the body and a free distal end opposite the proximate end. The distal end can have an aperture defined therein. The aperture can be sized and shaped to receive at least one human finger. A medical professional can extract the protective cover from the joint or implant site by grasping and pulling the free distal end of the tab with one or more fingers. Grasping the tab by inserting a finger through the aperture (i.e., finger hole) in the distal end of the tab reduces the likelihood that the tab will inadvertently slip from the grasp of the medical professional during extraction of the cover.

In another aspect, a protective cover for a prosthetic implant includes a domical body having a front side, a back side opposite the front side, a top portion, a bottom portion defining a lip, and a slit defined through a portion of the back side. In use, the body can prevent soft tissues from becoming adherent to a porous exterior surface of an acetabular cup received in the body during surgical introduction of the cup and cover into an acetabulum of a patient.

In yet another aspect, a protective cover for preventing soft tissues from becoming adherent to an exterior surface of an acetabular cup during surgical introduction of the cup into an acetabulum of a patient is provided. The protective cover includes a flexible, generally domical body. The body includes an axis of symmetry, a lip, a front side, a back side, an exterior surface, and an interior surface. The interior surface defines an interior space in which an acetabular cup is releasably receivable. The body also includes a slit or series of perforations defined through a portion of the back side of the body. The slit or series of perforations can extend from the lip to a location within $\pi/4$ radians (i.e., 45°) of the intersection of the axis with the exterior surface of the body.

The body is configured to cover substantially all of an exterior surface of the acetabular cup when the cup is received in the interior space, and to deform around and release the cup from the interior space into the acetabulum after the introduction of the cup and cover into the acetabulum upon the application of a pulling force to the front side of the body.

In still yet another aspect, a method for preventing soft tissues from becoming adherent to an exterior surface of a prosthetic implant during surgical introduction of the implant into a joint of a patient is provided. The method includes placing a prosthetic implant in a body of a protective cover configured to cover an exterior surface of the implant. The body of the protective cover includes a flexible domical portion having a lip, an exterior surface, an interior surface defining an interior space in which the prosthetic implant is receivable, and a slit extending through the body from the lip into the domical portion. The method further includes introducing the cup and protective cover into a joint of the patient and applying a pulling force to a side of the body opposite the slit to extract the cover over the implant and out of the joint of the patient.

Numerous other objects, advantages and features of the present disclosure will be readily apparent to those of skill in the art upon a review of the following drawings and description of a preferred embodiment.

BRIEF DESCRIPTION OF THE DRAWINGS

Non-limiting and non-exhaustive embodiments are described with reference to the following figures, wherein like reference numerals refer to like parts throughout the various drawings unless otherwise specified. In the drawings, not all reference numbers are included in each drawing, for the sake of clarity.

DETAILED DESCRIPTION

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the portions relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

This description and appended claims include the words "below", "above", "side", "top", "bottom", "upper", "lower", "when", "vertical", "horizontal", "upright", etc. to provide an orientation of embodiments of the invention to allow for proper description of example embodiments. The foregoing positional terms refer to the apparatus when in the orientation shown in FIG. 2. A person of skill in the art will recognize that the apparatus can assume different orientations when in use. It is also contemplated that embodiments of the invention may be in orientations other than upright without departing from the spirit and scope of the invention as set forth in the appended claims. Further, the terms "above", "below", "over", and "under" mean "having an elevation or vertical height greater or lesser than" and are not intended to imply that one object or component is directly over or under another object or component. The term "when" is used to specify orientation for relative positions of components, not as a temporal limitation of the claims or apparatus described and claimed herein unless otherwise specified.

The phrase "in one embodiment," as used herein does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Referring to FIGS. 1-4, in one embodiment, a protective cover 10 for a prosthetic implant 5 includes a thin, flexible body 12 having a height H, a lip 14, a central (i.e., top) portion 16, a back side 18, a front side 22 opposite the back side, an area of weakness 20 extending from the lip 14 into the central portion 16, an exterior surface 24, and an interior surface 26 that defines an interior space. The interior space has a diameter D and is configured (e.g., sized and shaped) to receive a prosthetic implant 5. The body 12 is configured to cover substantially all an exterior surface 6 of the prosthetic implant 5 when the implant is received in the interior space. In this way, the protective cover 10 advantageously prevents soft tissues (not pictured) through which the implant 5 is advanced during surgical introduction of the implant into a joint 2 of a patient in need of arthroplasty from contacting and becoming adherent to the exterior surface 6 of the implant.

Figure 7:
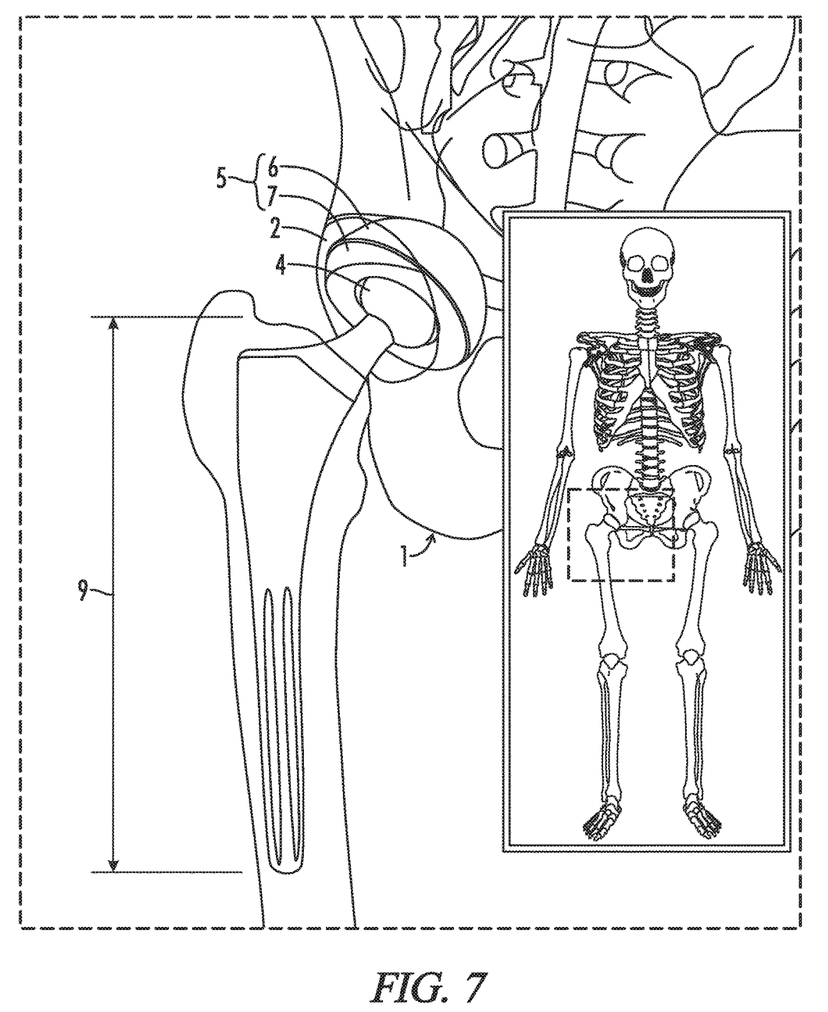
FIG. 7 is a diagram of a prosthetic implant with which the present invention can be advantageously used to prevent soft tissues through which the implant is advanced during surgical introduction of the prosthetic implant into a joint of a patient from contacting and becoming adherent to the exterior surface of the implant.

Although embodiments of the protective cover disclosed herein can be adapted for use with any prosthetic implant for which the prevention of contact between an exterior surface of the implant and soft tissues is necessary or desirable, the cover 10 disclosed herein is believed to be particularly useful to protect a hip prosthesis 5 from contact with surrounding soft tissues during total hip replacement surgery. FIG. 7 depicts a diagram of one embodiment of a prosthesis 5 with which use of the protective cover 10 disclosed herein is believed to be particularly advantageous received in a joint 2 of a human patient. The prosthetic implant 5 is an acetabular cup 5 having a porous, convex exterior or back surface 6 in the form of a shell, and a smooth, concave interior surface in the form of a liner or insert 7. The joint in which the acetabular cup 5 is fixed is an acetabulum 2 of the pelvis 1. The head 4 of a prosthetic femur (i.e., "stem") 9 is received in the insert 7.

Figure 8:
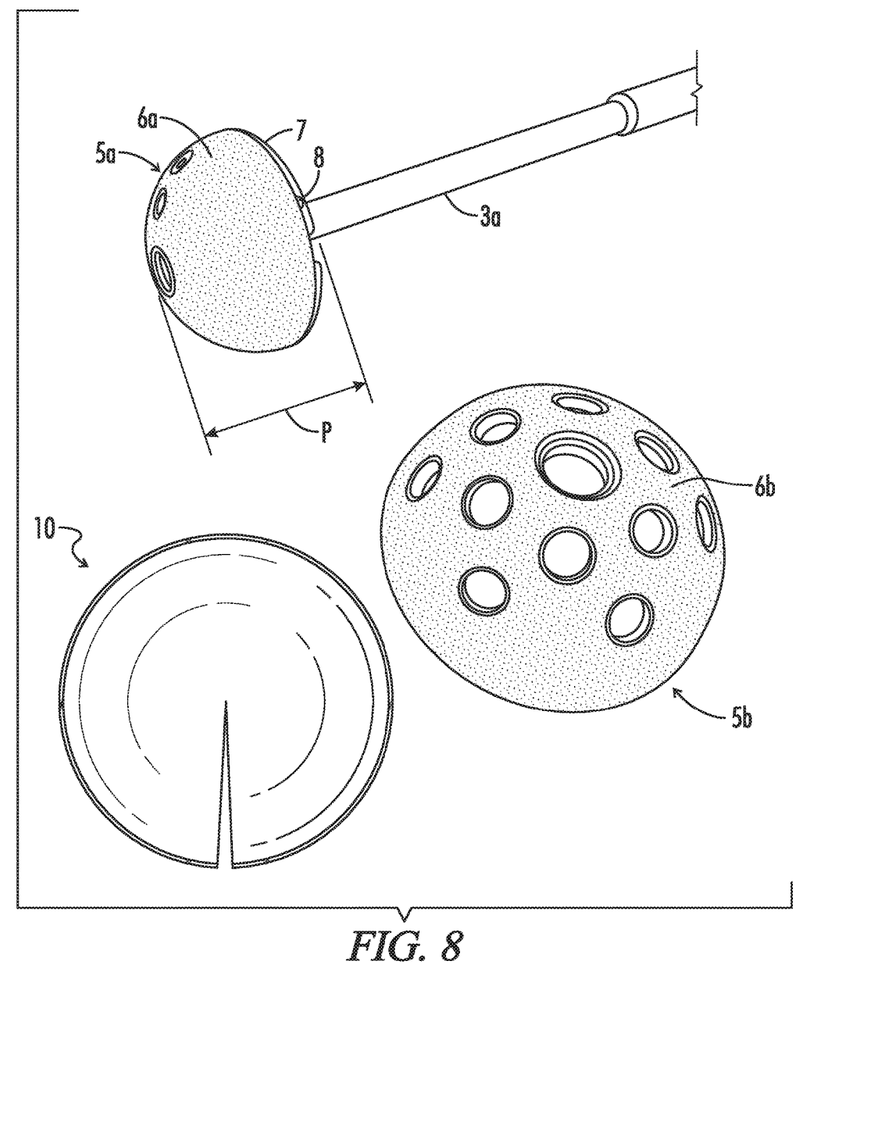
FIG. 8 is a perspective view of the protective cover of FIG. 1 alongside two prosthetic implants of different sizes.
Figure 9:
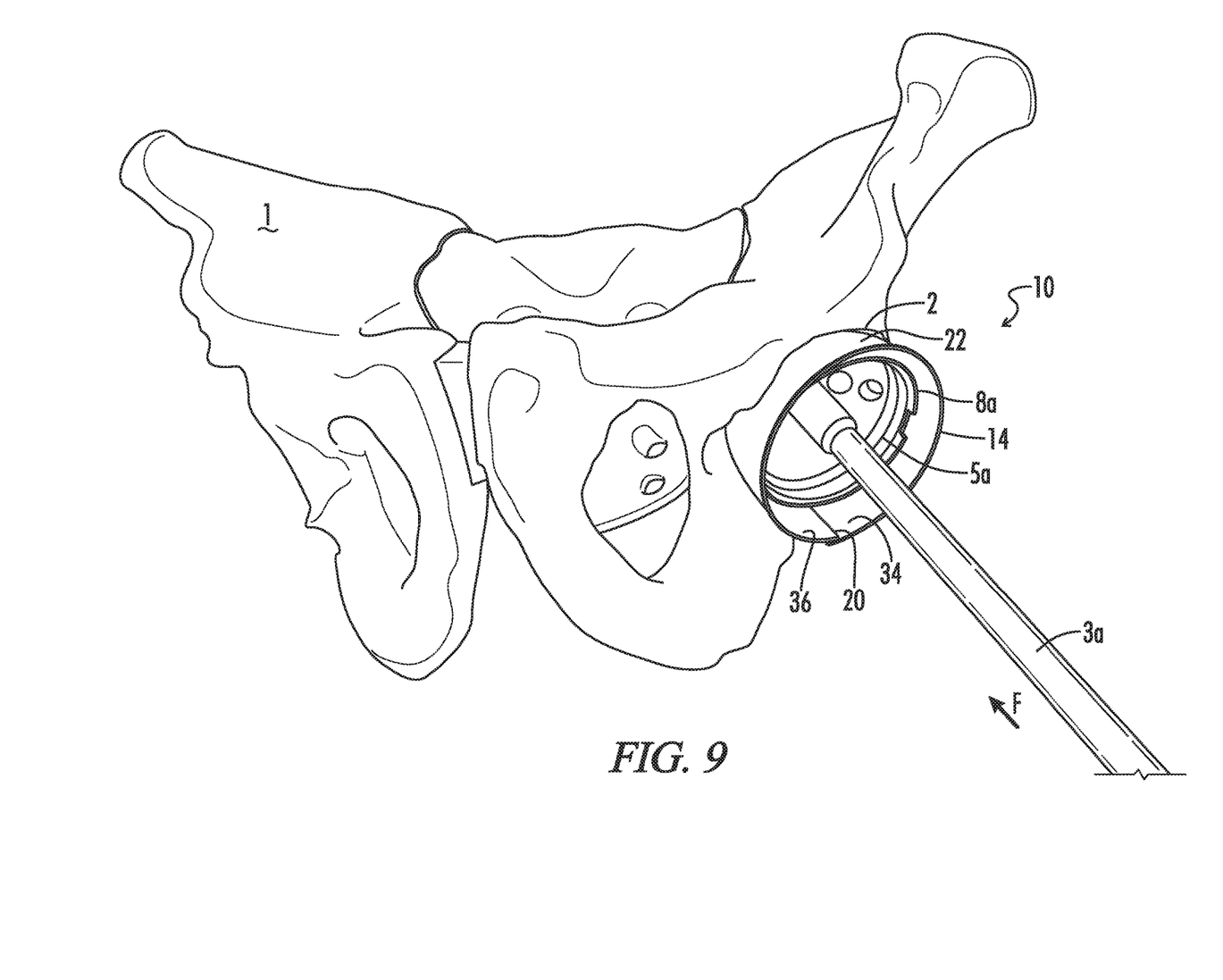
FIG. 9 is a perspective view of the protective cover of FIG. 1 illustrating use of the cover during introduction of an acetabular cup into the acetabulum of a human pelvis.

FIG. 8 depicts two additional embodiments 5a, 5b of acetabular cup 5 with different diameters alongside an embodiment of a protective cover 10. Acetabular cup 5a has a diameter smaller than the diameter of acetabular cup 5b. Acetabular cup 5a also has a diameter smaller than the diameter D of protective cover 10. As shown in FIGS. 8-9, the body 12 of the cover 10 is shaped and sized to cover substantially all the exterior surface 6a of acetabular cup 5a when the cup is received in the interior space of the body. As such, the interior surface of the body 12 can have a curvature that is complimentary to a curvature of an exterior surface 6a of the acetabular cup 5a. In some embodiments, the interior surface can also have a profile that is complimentary to a profile of the acetabular cup 5a.

Referring again to FIGS. 1-4, the body 12 can be generally domical (i.e., dome-shaped) and can have an axis of symmetry 28 around which the body is symmetrical. The intersection of the axis of symmetry 28 with the exterior surface 24 of the body 12 can define a pole 30. In some embodiments, the body 12 can include a hollow hemispherical portion having a radius. The central (i.e., top) portion 16 of the body 12 can be defined by a horizontally extending plane 32 spaced below the pole 30 about one half of the radius of the hemispherical portion of the body or less. The body 12 can have a height H that is greater than the height P of the prosthetic implant 5a so that a portion of the body extends beyond (i.e., overlaps) a rim 8 of the prosthetic implant when the implant is received in the interior space (see FIG. 9). Having a portion of the body 12 extend beyond the rim 8 of the implant 5a better protects the exterior surface 6a of the implant from contact with soft tissues which may otherwise seep or squeeze under the lip 14 of the cover 10 as the covered implant is advanced through an incision and underlying tissue.

Figure 1:
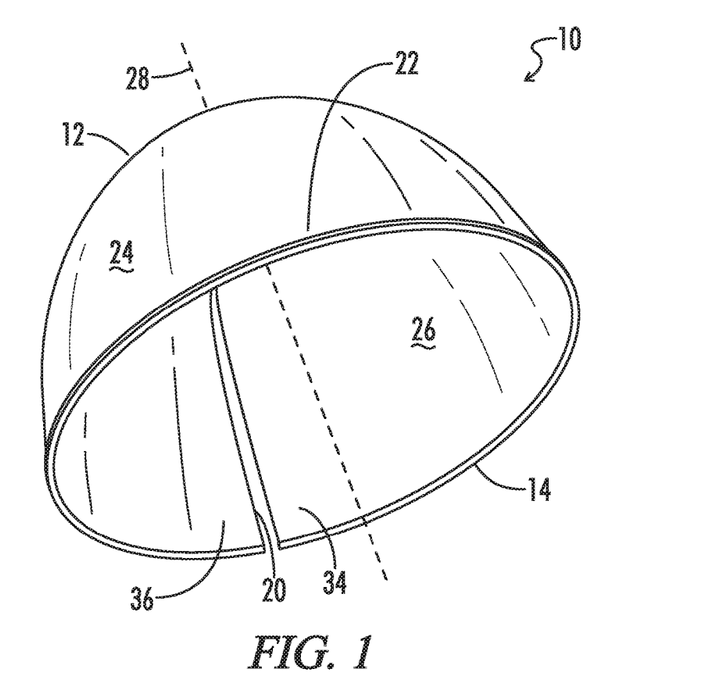
FIG. 1 is a depressed front perspective view of an embodiment of a protective cover for a prosthetic implant constructed in accordance with the present disclosure.
Figure 2:
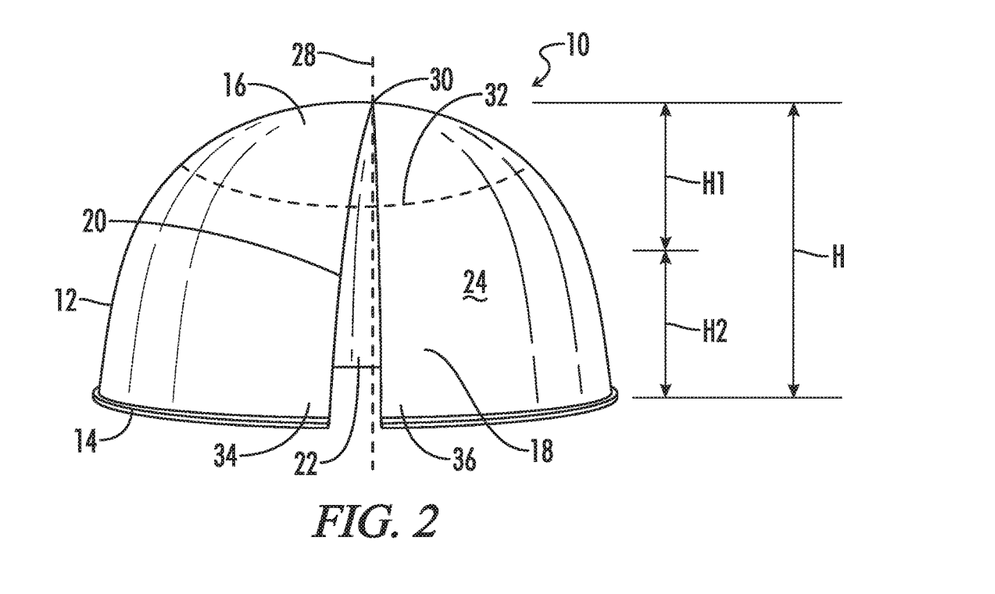
FIG. 2 is a rear elevational view of the protective cover of FIG. 1 showing the slit defined in the back side of the cover opened slightly wider than in FIG. 1.
Figure 3:
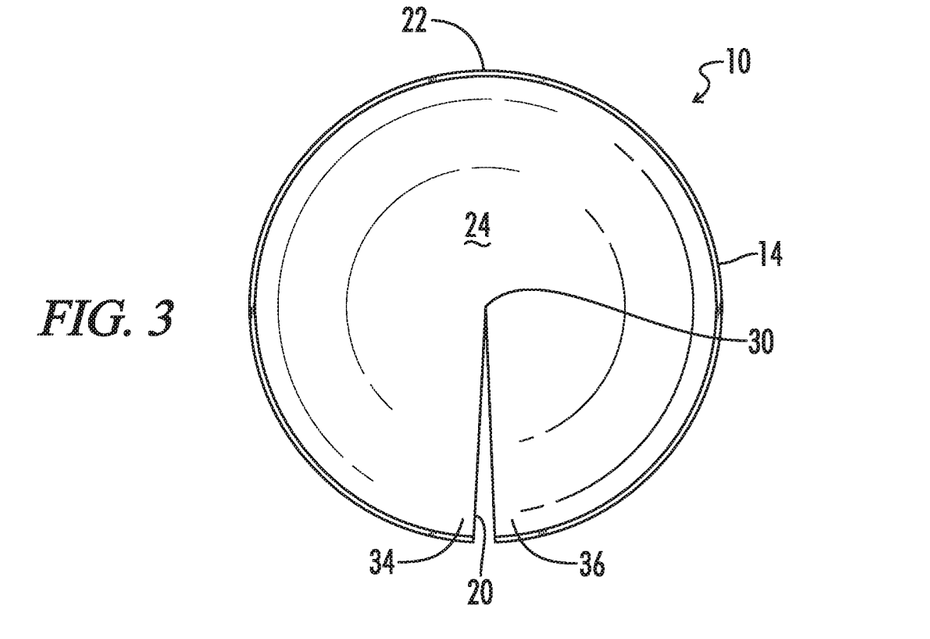
FIG. 3 is a top plan view of the protective cover of FIG. 1.
Figure 4:
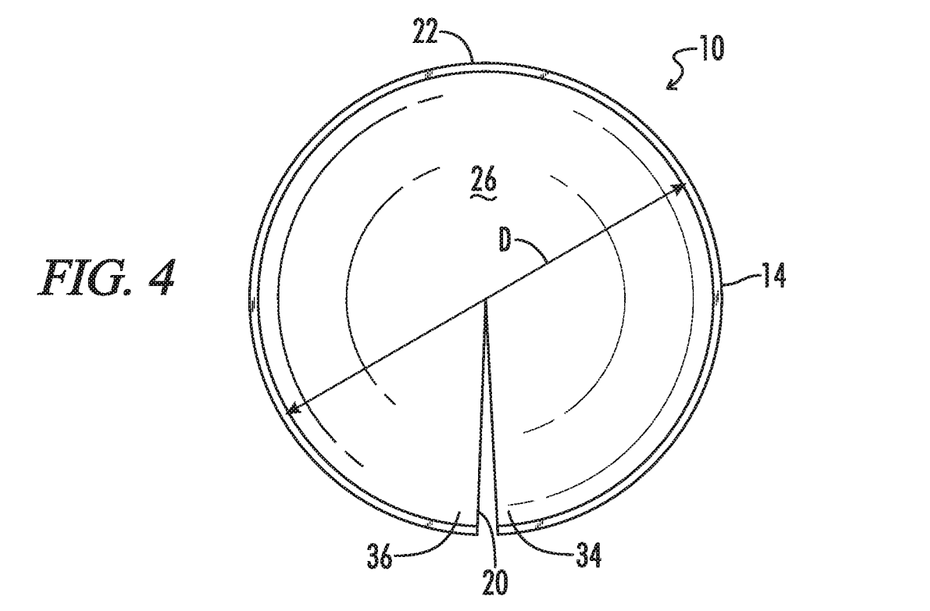
FIG. 4 is a bottom plan view of the protective cover of FIG. 1.

Accordingly, in some embodiments, the body 12 can also include a flared skirt portion extending from the edge of the hemispherical portion to the lip 14 such that the body 12 has the shape of a "deepen" hemisphere, as best shown in FIG. 2. The hemispherical portion can have a first height H1 and the skirt portion can have a second height H2 that is less than the first height H1. In such embodiments, the skirt portion can be the portion of the body 12 that extends beyond or overlaps the rim 8 of the implant 5a.

The body 12 can be configured to split or open along an area of weakness 20 (e.g., a narrow region or line of weakened structural integrity) and subsequently deform around the implant 5a to release the implant from the interior space through the area of weakness 20 upon the application of a pulling force F to a side 22 of the body opposite the area of weakness 20 when the implant is received in the interior space and the cover 10 is received in a joint 2 of a patient. As such, in some embodiments, the back side 18 of the body 12 includes an area of weakness 20 extending from the lip 14 into the central portion 16. The area of weakness 20 can be an area having a thinned cross section, a series of perforations, a slit 20 or the like, or a combination of any of an area having a thinned cross section, a series of perforations, a slit 20 and the like. In some embodiments, the area of weakness is a slit 20 extending through the body 12 in a line along an arc of the body from the lip 14 into the central (i.e., top) portion 16 of the body. In certain embodiments, the area of weakness is a slit 20 extending through the body 12 in a line along an arc of the body 12 from the lip 14 to a location within $\pi/4$ radians (i.e., 45°) of the intersection of the axis of symmetry 28 with the exterior surface 24 of the body (i.e., pole 30). In one embodiment, the area of weakness is a slit 20 extending through the body 12 in a line following an arc of the body from the lip 14 to the pole 30.

It should be noted that inclusion of an elongated slit 20 through the lip 14 and an adjacent portion 18 of the body 12 enables the interior space to effectively contract or expand to accommodate prosthetic implants 5 of different diameters, including implants having a diameter slightly greater or smaller than the diameter D of the interior space. Specifically, there is formed in the back side 18 of the body 12 on either side of the slit 20 a pair of highly flexible flaps 34, 36. When an implant 5a having a diameter slightly less than diameter D is received in the interior space, the flaps 34, 36 can move into an overlapping position as shown in FIG. 9 to effectively contract the interior space and still closely fit the implant 5a. By contrast, when an implant 5b having a diameter slightly greater than diameter D is received in the interior space, the flaps 34, 36 can flex outwardly (widening the slit 20) to effectively expand the interior space and still substantially cover the exterior surface 6b of the implant 5b. Accordingly, in some embodiments, the interior space can have a diameter D that ranges from slightly greater than to slightly lesser than the diameter of the prosthetic implant 5. For example, the diameter D of the interior space can be from about 10 mm to about 100 mm. In some embodiments, the diameter D of the interior space is from about from about 20 mm to about 80 mm. In some specific embodiments, the diameter D of the interior space can be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 mm.

Figure 10:
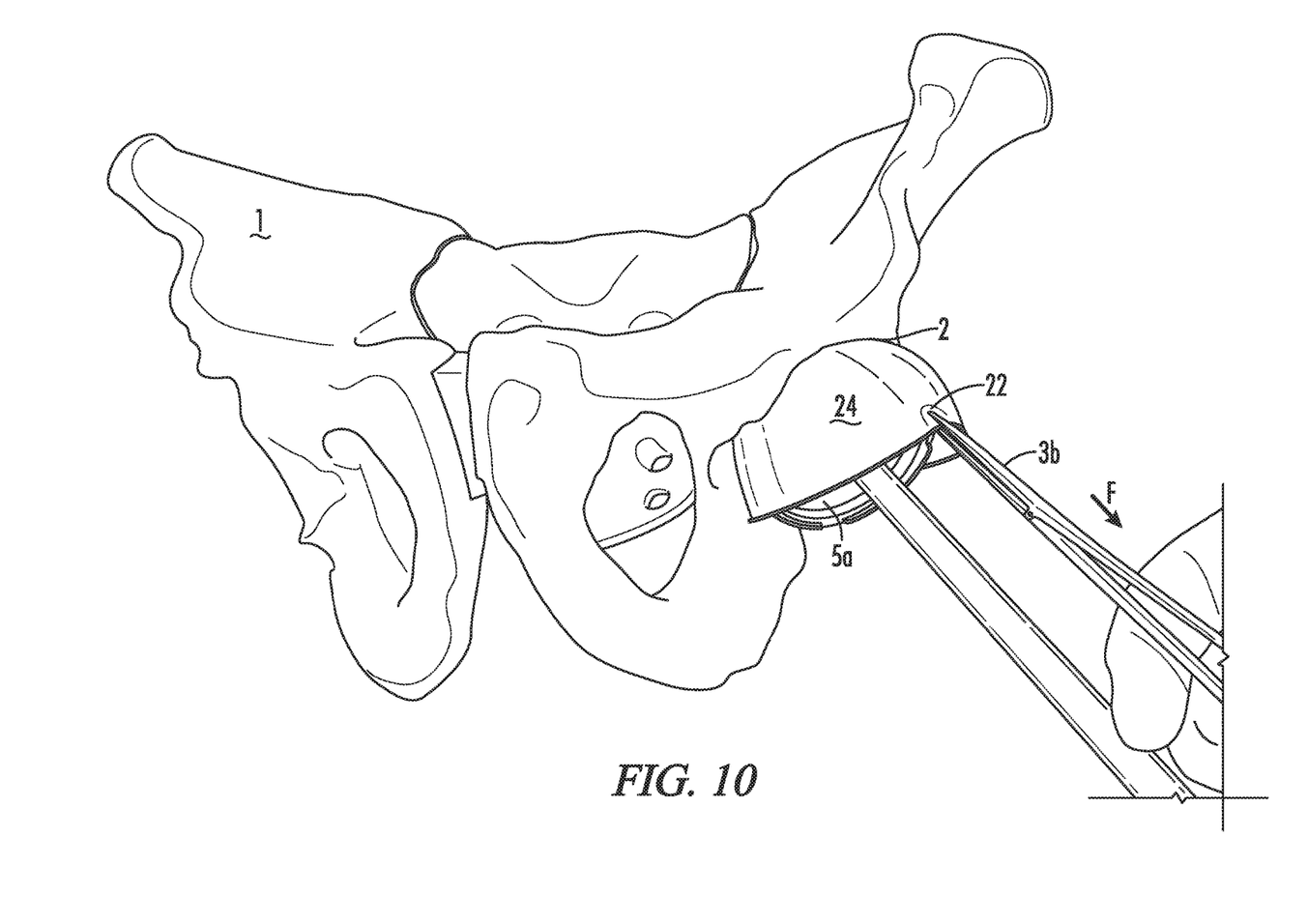
FIG. 10 is a perspective view of the protective cover of FIG. 1 partially extracted from the acetabulum of a human pelvis after introduction of an acetabular cup into the acetabulum using the cover.
Figure 11:
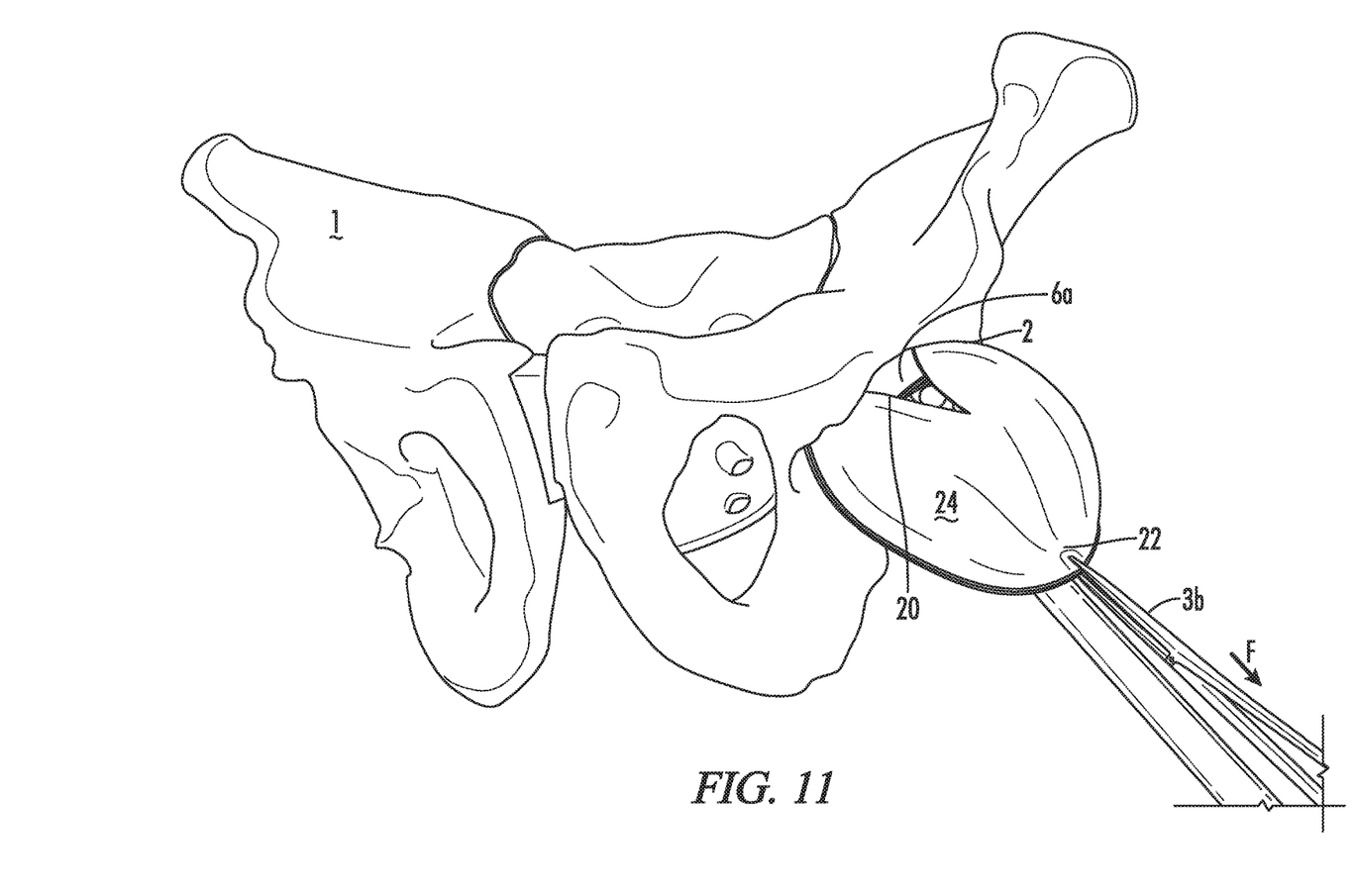
FIG. 11 is another perspective view of the protective cover of FIG. 1 further extracted from the acetabulum of a human pelvis after introduction of an acetabular cup into the acetabulum using the cover.
Figure 12:
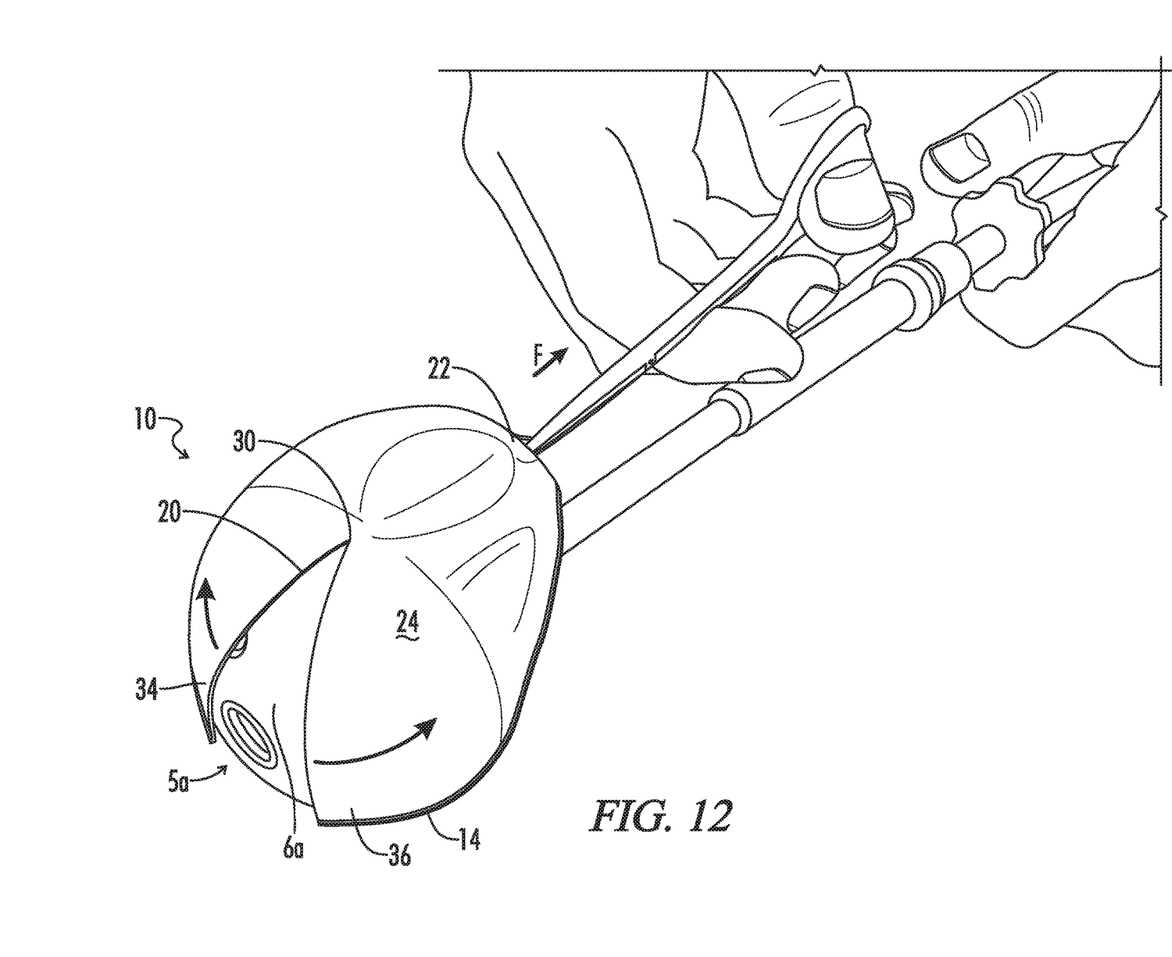
FIG. 12 is a rear perspective view of the protective cover of FIG. 1 illustrating deformation of the cover and expansion of the slit around an acetabular cup during extraction of the cover from the acetabulum of a human pelvis.

It is to be understood that the area of weakness 20 can be any structure or narrow opening 20 that permits the back side 18 of the flexible body 12 to open and deform around the prosthetic implant 5a (as best shown in FIG. 12) during extraction of the cover 10 from a joint 2 of a patient into which the implant has been introduced while received in the interior space of the cover 10. As best shown in FIGS. 10-12, the cover 10 can be extracted from the joint 2 after introduction of the implant 5a therein by applying a pulling force F to a side of the body 12 generally opposite the area of weakness 20 (i.e., front side 22) and moving (i.e., pulling) the body in a direction away from and out of the joint 2. The pulling force F can be manually applied to the body 12 using fingers or a grasping surgical instrument 3b, such as a clamp or forceps 3b.

Figure 5:
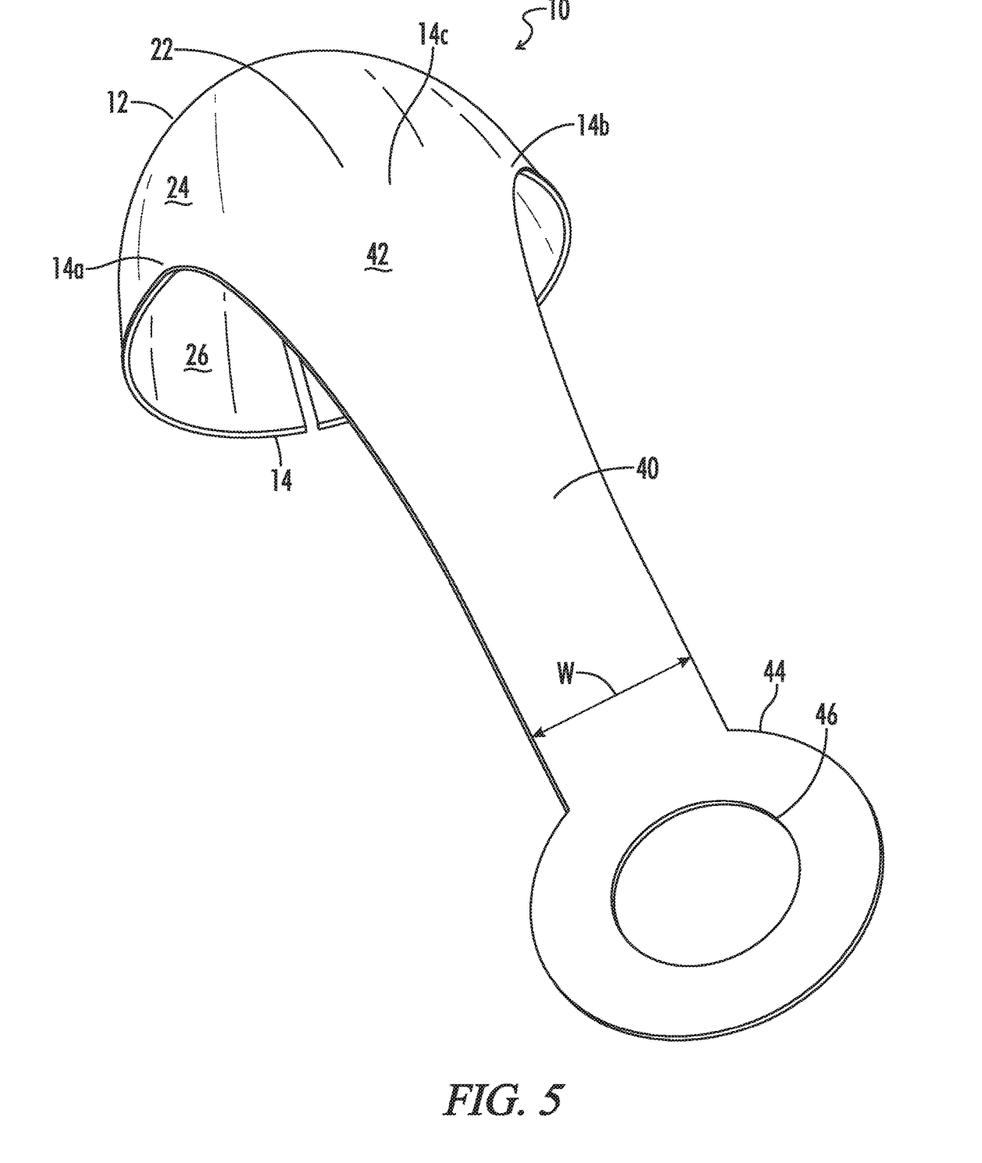
FIG. 5 is a depressed front perspective view of another embodiment of a protective cover for a prosthetic implant constructed in accordance with the present disclosure.
Figure 6:
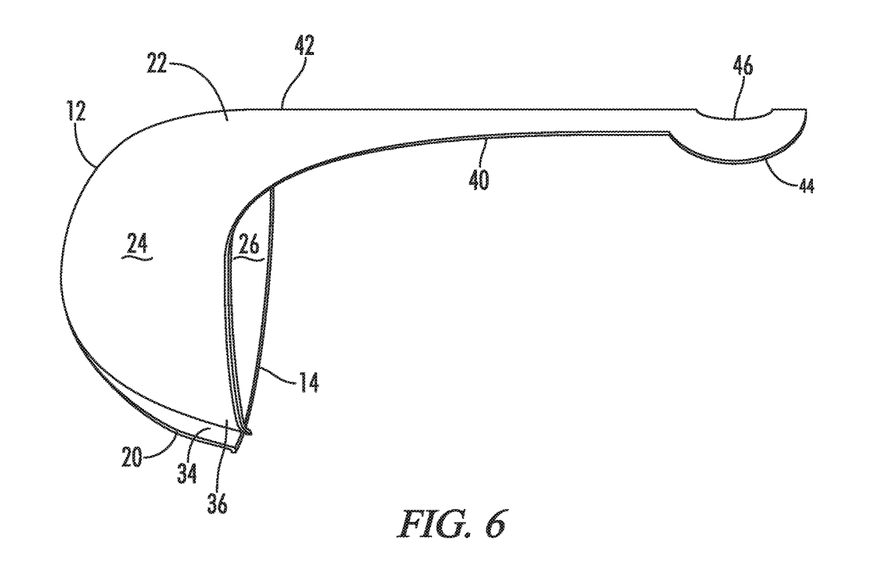
FIG. 6 is an elevated side perspective view of the protective cover of FIG. 5.

Referring now to FIGS. 5-6, in another embodiment, the protective cover 10 can include an elongated tab 40 extending from a portion of the body 12 to facilitate extraction of the cover 10 from a joint 2. The tab 40 can be configured to assist a medical professional with manually grasping and extracting the protective cover 10 from a joint 2 of a patient after the cover 10 has been used to introduce a prosthetic implant into the joint. The tab 40 can have a width W, a proximate end 42 adjacent to the body 12, and a free distal end 44 opposite the proximate end 42 for grasping by a medical professional during extraction of the cover 10 from the joint 2. The width W can be uniform throughout the length of the tab 40. In some embodiments, the width W of can be non-uniform throughout the length of the tab 40. In a specific embodiment, the proximate 42 of the tab 40 can have a width that is greater than the width of the distal end 44.

The proximate end 42 can extend from any portion of the body 12, but in preferred embodiments, extends from a side of the body 12 opposite the area of weakness 20, such as, for example, the front side 22. In some embodiments, the portion of the front side 22 from which the proximate end 42 extends includes a midpoint 14c of the lip 14 located directly opposite the area of weakness 20 (i.e., half way around the perimeter of the lip 14 from the area of weakness 20). In some embodiments, the portion of the lip 14 from which the proximate end 42 of the tab 40 extends can include an arc of the lip 14 extending from a first lip position 14a to a second lip position 14b spaced around a perimeter of the lip 14 from the first lip position 14a. The second lip position 14b can be spaced from about $\pi/12$ radians (15°) to about $\pi$ radians (180°) around a perimeter of the lip 14 from the first lip position 14a. In more particular embodiments, the arc of the lip from which the tab 40 extends includes midpoint 14c. In a preferred embodiment, the width W of the tab 40 is centered on the midpoint 14c of the lip 14 such that the opposing edges of tab 40 correspond to the first and second lip positions 14a, 14b and the first and second lip positions 14a, 14b are equidistantly spaced around the perimeter of the lip 14 from the area of weakness or slit 20. This positioning of tab 40 on lip 14 relative to slit 20 aids in extraction of the protective cover 10 from the joint 2 of a patient by distributing the pulling force F used to extract the cover along a greater portion of the lip 14 and thus body 12. The distribution of pulling force F in turn causes flaps 34, 36 to more readily open as the body 12 is pulled over the prosthetic implant during extraction of the cover 10 from the joint 2. Accordingly, in some embodiments, the tab 40 can advantageously have a width W that is approximately equal to one-half the perimeter or circumference of the lip 14. In other embodiments, the tab 40 can have a width W that is less than one-half the perimeter or circumference of the lip 14.

The tab 40 can include an aperture (i.e., hole) 46 defined through the free distal end 44. The aperture 46 can be shaped and sized to receive one or more human fingers. The tab 40 can be any length, but is preferably long enough that the distal end 44 extends out of the body or person of a patient when the cover 10 is received in the joint 2 so that a medical professional can grasp the tab 40 without the aid of a grasping surgical instrument 3b such as forceps 3b. For example, in some embodiments, the tab 40 can be from about 5.0 cm to about 40.0 cm or more long. In some preferred embodiments, the tab 40 can be about 10.0 cm to about 30 cm long. In some specific embodiments, the tab 40 is about 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30 cm long.

The protective cover 10 disclosed herein, including the body 12 and the tab 40 (for embodiments including a tab), can be formed from any flexible, slick material that allows a prosthetic implant 5a received in the interior space of the cover 10 to smoothly pass through the soft tissues surrounding the joint 2 to be replaced. The material should also be durable enough to withstand direct contact with bone without tearing, as well as the forces required to extract the protective cover 10 in one piece from behind the prosthetic implant 5a once the implant has been introduced into the desired joint 2 of a patient. As such, the protective cover 10 disclosed herein can be formed form a polymeric material, such as a plastic. In some embodiments, the body 12 of the protective cover 10 can have a thickness of from about 0.050 mm to about 2.500 mm. For example, in some embodiments, the body can have a thickness of about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.05, 2.10, 2.15, 2.20, 2.25, 2.30, 2.35, 2.40, 2.45, or 2.50 mm. It is to be understood, however, that the thickness of the body 12 can differ depending on the flexibility and durability of the constituent polymeric material selected to form the body. It is also to be understood that tab 40 can be formed from the same or a different material from body 12, and that the thickness of tab 40 can differ from the thickness of body 12.

Use of a protective cover 10 of the present disclosure is illustrated by reference to FIGS. 8-12, wherein a prosthetic implant in the form of an acetabular cup 5a is shown releasably connected to a surgical instrument 3a configured to facilitate advancement of the acetabular cup 5a through soft tissue surrounding an acetabulum 2 of a pelvis 1 in need of replacement.

The acetabular cup 5a can be placed in the interior space of a protective cover 10 configured to cover an exterior surface 6a of the acetabular cup 5a. With the acetabular cup 5a received in the interior space, the cup 5a can be introduced into the patient through an incision (not shown) in the hip region and advanced through the soft tissues (not shown) surrounding the pelvis 1 into the acetabulum 2 by the application of forward force F to instrument 3a, as indicated in FIG. 9.

Once the acetabular cup 5a has been introduced into the level of the acetabulum 2 bone, the protective cover 10 can be extracted from the acetabulum 2 and the acetabular cup 5a simultaneously released from interior space of body 12 by applying a rearward pulling force F to (e.g., pulling) a side 22 of the body 12 opposite the slit 20, as indicated in FIGS. 10-11. The application of a pulling force F to the cover 10 in a direction away from and out of the joint 2 causes the flexible body 12 to deform and the slit or area of weakness 20 defined therein to open around the acetabular cup 5a as the cover is pulled over the cup 5a and out of the joint, as best shown in FIGS. 11-12.

Although embodiments of the present invention have been described in detail, it will be understood by those skilled in the art that various modifications can be made therein without departing from the spirit and scope of the invention as set forth in the appended claims. For example, although the invention has been described in the context of use as a protective cover for an acetabular cup 5 during introduction of the cup into an acetabulum 2 of the pelvis bone 1 of a patient, it is to be understood that the invention disclosed herein can also be used with other prosthetic implants during introduction of such an implant into a different joint of a patient. Further, it is to be understood that the invention is not limited to use with prosthetic implants for humans. It is specifically contemplated that the invention may also be used to introduce a prosthetic implant into a joint of an animal.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful PROTECTIVE COVER FOR A PROSTHETIC IMPLANT, it is not intended that such references be construed as limitations upon the scope of this invention except as set forth in the following claims.

What is claimed is:

1. A protective cover for a prosthetic implant, comprising:
   a flexible body having a central portion, a lip, an exterior surface, and an interior surface, the interior surface defining an interior space in which a prosthetic implant is receivable; and
   an area of weakness formed in the body and extending from the lip into the central portion;
   wherein the body covers substantially all of an exterior surface of the prosthetic implant when the implant is received in the interior space; and
   wherein a curvature of the interior surface of the body is complimentary to a curvature of the exterior surface of the prosthetic implant.

2. The cover of claim 1, wherein the body is configured to open along the area of weakness and deform around the implant to release the implant from the interior space through the area of weakness upon the application of a pulling force to a side of the body opposite the area of weakness when the implant is received in the interior space and the cover is received in a joint of a patient.

3. The cover of claim 1, wherein the area of weakness extends along an arc of the body from the lip into the central portion and comprises a thinned cross section, a series of perforations, or a slit.

4. The cover of claim 1, wherein the body prevents substantially all the exterior surface of the implant received in the interior space from contacting soft tissues through which the implant is advanced during surgical introduction of the implant into a joint of a patient.

5. The cover of claim 1, wherein a portion of the body extends beyond a rim of the prosthetic implant when the implant is received in the interior space.

6. The cover of claim 1, wherein the body includes a hollow, substantially hemispherical portion having an axis of symmetry and a pole defined by the intersection of the axis with the exterior surface of the body.

7. The cover of claim 6, wherein the central portion of the body is defined by a horizontally extending plane spaced less than one half of a radius of the hemispherical portion of the body below the pole.

8. The cover of claim 6, wherein the area of weakness extends from the lip to the pole.

9. The cover of claim 6, wherein the body further includes a skirt portion extending from the hemispherical portion to the lip.

10. The cover of claim 9, wherein:
    the hemispherical portion has a first height;
    the skirt portion has a second height; and
    the second height is less than the first height.

11. The cover of claim 1, further comprising an elongated tab extending from a side of the body opposite the area of weakness.

12. The cover of claim 11, wherein the tab extends from a portion of the lip opposite the area of weakness.

13. The cover of claim 12, wherein:
    the tab includes a proximate end extending from the lip and a free distal end opposite the proximate end;
    the distal end includes an aperture through which a human finger is removably receivable; and
    the portion of the lip from which the proximate end of the tab extends comprises an arc of the lip extending from a first lip position to a second lip position spaced from about $\pi/12$ radians (15°) to about $\pi$ radians (180°) around a perimeter of the lip from the first lip position.

14. The cover of claim 13, wherein:
    the arc includes a midpoint of the lip; and
    the proximate end of the tab is centered on the midpoint.

15. A protective cover for a prosthetic implant, comprising:
    a domical body having a front side, a back side opposite the front side, a top portion, a bottom portion defining a lip, and a slit defined through a portion of the back side, the slit extending from the lip into the top portion of the body;

wherein the body prevents soft tissues from becoming adherent to a porous exterior surface of an acetabular cup received in the body during surgical introduction of the cup and cover into an acetabulum of a patient.

16. The cover of claim 15, further comprising an elongated tab extending from a portion of the lip located on the front side of the body, the tab having an aperture defined therein, the aperture sized and shaped to receive a human finger.

17. The cover of claim 16, wherein the body deforms around the acetabular cup and thereby releases the cup through the slit into the acetabulum of the patient upon the application of a pulling force to the tab in a direction away from the acetabulum after the cup and cover have been introduced into the acetabulum.

18. The cover of claim 15, wherein:
 a portion of the body extends beyond a rim of the acetabular cup when the cup is received in the body; and
 the body prevents the porous exterior surface of the acetabular cup received in the body from contacting soft tissues surrounding the acetabulum of the patient during surgical introduction of the cup into the acetabulum.

19. A protective cover for a prosthetic implant, comprising:
 a flexible body having a central portion, a lip, an exterior surface, and an interior surface, the interior surface defining an interior space in which a prosthetic implant is receivable; and
 an area of weakness formed in the body and extending along an arc of the body from the lip into the central portion;
 wherein the area of weakness comprises a thinned cross section, a series of perforations, or a slit; and
 wherein the body covers substantially all of an exterior surface of the prosthetic implant when the implant is received in the interior space.

20. The cover of claim 19, further comprising an elongated tab extending from a portion of the lip opposite the area of weakness, wherein the tab includes an aperture through which a human finger is removably receivable.

* * * * *